(12) United States Patent
Pei et al.

(10) Patent No.: US 7,668,593 B1
(45) Date of Patent: Feb. 23, 2010

(54) SYSTEM AND METHOD TO ACCELERATE INDIVIDUALIZED GAIN ADJUSTMENT IN IMPLANTABLE MEDICAL DEVICE SYSTEMS

(75) Inventors: Xing Pei, Thousand Oaks, CA (US); Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 185 days.

(21) Appl. No.: 11/694,534

(22) Filed: Mar. 30, 2007

(51) Int. Cl.
*A61N 1/36* (2006.01)

(52) U.S. Cl. .......................................................... 607/7
(58) Field of Classification Search ........................ 607/7
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,940,052 A | 7/1990 | Mann et al. | |
| 5,197,467 A | 3/1993 | Steinhaus et al. | |
| 5,273,049 A | 12/1993 | Steinhaus et al. | |
| 5,300,093 A | 4/1994 | Koestner et al. | |
| 5,374,282 A * | 12/1994 | Nichols et al. | 607/18 |
| 5,458,621 A * | 10/1995 | White et al. | 607/5 |
| 5,466,254 A | 11/1995 | Helland | |
| 5,476,483 A | 12/1995 | Bornzin et al. | |
| 5,555,888 A | 9/1996 | Brewer et al. | |
| 5,573,550 A | 11/1996 | Zadeh et al. | |
| 5,662,688 A * | 9/1997 | Haefner et al. | 607/5 |
| 5,694,943 A | 12/1997 | Brewer et al. | |
| 5,718,720 A | 2/1998 | Prutchi et al. | |
| 5,957,857 A | 9/1999 | Hartley | |
| 6,275,734 B1 * | 8/2001 | McClure et al. | 607/27 |
| 6,314,323 B1 | 11/2001 | Ekwall | |
| 6,363,277 B1 | 3/2002 | Dooley et al. | |

(Continued)

FOREIGN PATENT DOCUMENTS

| WO | 03043693 A3 | 5/2003 |
|---|---|---|
| WO | WO03/043693 A2 | 5/2003 |

OTHER PUBLICATIONS

Ebner, Erich et al., "Ventricular Evoked Response as Clinical Marker for Hemodynamic Changes in Dilative Cardiomyopathy," PACE. 2004;27:166-174.

(Continued)

*Primary Examiner*—Carl H Layno
*Assistant Examiner*—Jeremiah T Kimball

(57) ABSTRACT

A system and method for increasing the speed of individualizing amplifier gain optimization in implantable medical devices. A variable amplifier gain is initially set at a relatively high level such that the amplifier experiences at least intervals of saturation. A saturation indicator is determined which is indicative of the relative degree of saturation. The gain is then adjusted as a function of the saturation indicator. Relative larger degrees of saturation result in more aggressive gain adjustment. This increases the speed of adjustment with reduced likelihood of loss of sensing. In one implementation, one or more discrete amplifier gain adjustment steps are made in a single adjustment to effectively skip over intermediate adjustments. In another implementation, an estimate is made of a signal peak during a saturating interval. The gain is adjusted directly based on the estimated peak with appropriate sensing safety margins. The method can be implemented with a system including a programmer in communication with an implantable device.

10 Claims, 11 Drawing Sheets

U.S. PATENT DOCUMENTS

| | | | |
|---|---|---|---|
| 6,389,315 | B1 | 5/2002 | Schu et al. |
| 6,415,181 | B1 | 7/2002 | Schu et al. |
| 6,438,409 | B1 | 8/2002 | Malik et al. |
| 6,456,880 | B1 | 9/2002 | Park et al. |
| 6,473,647 | B1 | 10/2002 | Bradley |
| 6,512,953 | B2 | 1/2003 | Florio et al. |
| 6,531,907 | B2 | 3/2003 | Dooley et al. |
| 6,539,259 | B1 | 3/2003 | Weinberg et al. |
| 6,745,076 | B2 * | 6/2004 | Wohlgemuth et al. ......... 607/27 |
| 6,865,421 | B2 | 3/2005 | Bradley |
| 7,078,966 | B2 * | 7/2006 | Khlat et al. ................. 330/129 |
| 2002/0087146 | A1 | 7/2002 | Schu et al. |
| 2003/0097157 | A1 | 5/2003 | Wohlgemuth et al. |
| 2004/0230242 | A1 | 11/2004 | van Dam et al. |

OTHER PUBLICATIONS

NonFinal Office Action, mailed Apr. 4, 2007: Related U.S. Appl. No. 10/997,611.

Final Office Action, mailed Oct. 31, 2007: Related U.S. Appl. No. 10/997,611.

NonFinal Office Action, mailed Feb. 11, 2008: Related U.S. Appl. No. 10/997,611.

Final Office Action, mailed Dec. 11, 2008: Related U.S. Appl. No. 10/997,611.

* cited by examiner

| Saturation Ratio SR | Gain Adjustment (steps per adjustment) |
|---|---|
| 0 | No adjustment |
| 0--30% | 1 |
| 31-60% | 2 |
| 61-85% | 3 |
| 86-100% | 4 |

SYSTEM AND METHOD TO ACCELERATE INDIVIDUALIZED GAIN ADJUSTMENT IN IMPLANTABLE MEDICAL DEVICE SYSTEMS

BACKGROUND OF THE INVENTION

1. Field of the Invention

The invention relates to the field of implantable medical device systems and, more particularly, to systems and methods to improve the efficiency or speed of adjusting or "optimizing" the gain settings of the implantable medical device systems for individual patients.

2. Description of the Related Art

Implantable medical device systems have been developed to treat a wide variety of patient health ailments. One particular type of implantable medical device system includes implantable pacemakers and implantable cardioverter-defibrillators (ICDs) which are configured to automatically monitor the patient and selectively provide appropriate therapy for a variety of cardiac arrhythmias. Implantable cardiac stimulation devices, such as pacemakers and/or ICDs are available in a wide variety of configurations and are typically further individualized for the particular needs of a given patient. This is typically implemented by selecting an appropriate configuration of implantable cardiac stimulation device for the patient and further customizing that particular configuration by programming a plurality of operating characteristics or parameters of the device.

Programming of the device typically initially takes place in a clinical setting where a physician implants the device, affixes one or more patient leads, and performs an initial programming of the device. This procedure is typically assisted by other attending clinical personnel as well as with a physician's programmer which establishes telemetric communication with the device being implanted. The programmer allows the clinician to communicate with the device both for providing programming and other data commands as well as to interrogate the device, for example to extract data indicative of the device's performance and configuration. As may be expected with a relatively complex medical therapy system, a number of parameters or operating characteristics must generally be set, verified, evaluated, and frequently adjusted. One particular type of operating characteristic or parameter which generally needs to be individually adjusted for the particular patient and device are amplifier gain settings.

Amplifiers typically have a dynamic range and in implantable medical device applications, this dynamic range is generally adjustable. In general, the dynamic range of amplifiers is preferably adjusted to employ a substantial portion of the available dynamic range of the amplification, however, also adjusted to avoid saturation of the amplifier. Employing a substantial amount of the dynamic range available improves the discernable resolution of the amplified signal which facilitates more precise evaluation of a sensed signal. Saturation of the amplifier is preferably avoided as during periods of saturation, the magnitude of the amplified signal is no longer proportional to the input signal.

Saturation occurs when the amplifier can no longer provide a proportional amplified signal as the output of the amplifier reaches a maximum output value.

The amplitude multiplication or amplification factor of the input signal provided by the amplifier is referred as the gain. When the amplitude of the input signal multiplied by the current gain exceeds the maximum amplifier output, amplifier saturation occurs. Thus, the gain would be adjusted lower for a given input signal to bring the amplification of the input signal within the available maximum amplifier output so to fit within the available dynamic range. This is also referred to as adjusting the sensitivity of the system. System sensitivity is the complement of gain of the amplifier, e.g. an increase in sensitivity corresponds to a decrease in gain.

This process of adjusting the gain of an amplifier to employ a substantial portion of the available dynamic range while avoiding saturation conditions is generally referred to in the field as "gain optimization." As used herein, the terms "optimization" or "optimizing" are terms of the art and refer simply to a process of evaluating and adjusting or individualizing the operating parameters of an amplifier system for improved sensing of the expected signals. Optimizing or optimization does not imply that this process results in a perfect setting for the system or that further improvements are not available. Thus, optimizing and optimization are to be interpreted as relative terms and not as absolutes.

In particular, as signals frequently provided to the amplifiers for amplification are of a physiologic origin, they are subject to variation that is frequently subject to change on a cycle to cycle basis, on a diurnal basis, and on an aperiodic or unpredictable basis. It is thus frequently preferable to provide at least some safety margin in the setting of the dynamic range to accommodate unusually low or high input signal levels. Gain optimization in the context of sensing physiologic signals is a matter of compromise and balancing multiple factors to achieve improved, but not necessarily perfect performance.

A gain adjustment or optimization procedure generally proceeds in an interactive manner with the physician throughout a process of iterative adjustment of the gain settings and observation and analysis of the adjusted amplification output. A typical procedure for evaluating and adjusting or optimizing the amplifier gain for a particular patient and device typically encompasses an interval of 20-30 seconds up to several minutes. This constitutes "dead time" for the attending clinician as limited other aspects of the programming of the device can generally take place while the gain optimization procedure is being conducted. As physicians and other clinical personnel are highly trained and compensated personnel, it is desirable that efficient use be made of their time during the implantation procedure. Physicians have reported frustration with extended durations of gain optimization procedures as they are in many existing implementations effectively forced to wait until the gain optimization process concludes before proceeding with further tasks in the initial implant and programming procedure.

SUMMARY OF THE INVENTION

Thus, it will be appreciated that there is a desire and need for improvements in the individualized adjustments or optimization of amplifier gain for implantable medical device systems. More particularly, there is a need and desire to reduce the dwell time of a gain adjustment procedure to thereby reduce the down or dead time for the attending clinician while maintaining the advantages of individualized adjustment of an implantable device system for individual patients.

These needs are satisfied by the invention in which one embodiment is a method of adjusting amplifier gain in an implantable medical device, the method comprising positioning at least one sensing electrode to sense at least one physiologic signal, amplifying the at least one physiologic signal at a first gain setting wherein the first gain setting, are usually high to avoid under-sensing, results in at least intervals of amplifier saturation, determining a relative saturation indicator for the first gain setting and adjusting the first gain setting to a second gain setting based at least partially on the determined relative saturation indicator such that the second gain setting avoids saturation with expected amplitudes of the at least one physiologic signal.

Another embodiment is an implantable medical device system comprising an implantable sensing electrode configured to sense one or more physiologically based signals, at least one signal amplifier receiving the physiologically based signals and amplifying these signals by an adjustable amplifier gain, and a controller receiving the amplified signals and evaluating a patient's condition as indicated by the amplified signals, wherein, following an initial implantation, the amplified signals are evaluated and a saturation indicator is calculated and wherein the amplifier gain is adjusted as a function of the saturation indicator so as to inhibit saturation of the signal amplifier with larger saturation indicators resulting in more aggressive gain adjustment.

A further embodiment is a method of selecting an appropriate gain setting for a signal amplifier for an implanted cardiac stimulation device, the method comprising (i) receiving a signal indicative of function of a patient's heart wherein the signal is amplified by an amplifier of the implanted cardiac stimulation device, (ii) selecting at least one characteristic of the signal and calculating a saturation parameter based upon the at least one selected characteristic of the patient's heart, (iii) automatically determining a gain adjustment value that correlates, at least in part, to the magnitude of the saturation parameter, and (iv) adjusting the gain of the amplifier by the gain adjustment value. These and other objects and advantages of the invention will become more apparent from the following description taken in conjunction with the accompanying drawings.

DETAILED DESCRIPTION

Reference will now be made to the drawings wherein like numerals refer to like parts throughout. The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1A:
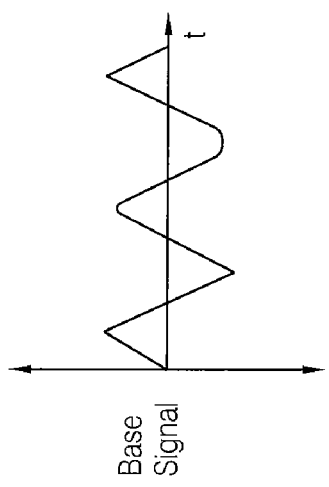
FIGS. 1A-1D illustrate exemplary waveforms of a base signal and various amplified waveforms with varying gain settings.

FIGS. 1A through 1D are highly simplified waveforms illustrating certain aspects of the context in which the preferred embodiments of the invention operate. FIG. 1A illustrates a highly simplified base signal which may be sensed by an implantable medical device. The base signal illustrated in FIG. 1A would generally in practice comprise a much more complex waveform morphology and could correspond, for example, to nerve signals, cardiac depolarization, transthoracic impedance, or any number of other physiologically based signals which may be of interest to the particular application. FIG. 1A illustrates generally, however, that the base signal would typically vary in a generally cyclical manner and is shown having both positive and negative excursions from a base line or zero level. In many implantable device applications, the amplitude of the base signal as initially sensed is too low for effective evaluation and processing without some degree of amplification and thus the previously described amplifiers are generally provided to amplify the base signals for subsequent processing. It will be understood that for improved evaluation of the base signal, any amplification applied to the base signal should substantially retain the signal's fidelity, such as by accurately maintaining the relative proportions or morphology of the signal following the amplification process. It is also generally desirable to use a substantial portion of the dynamic range of amplifiers to facilitate analysis of the amplified signal.

Figure 1D:
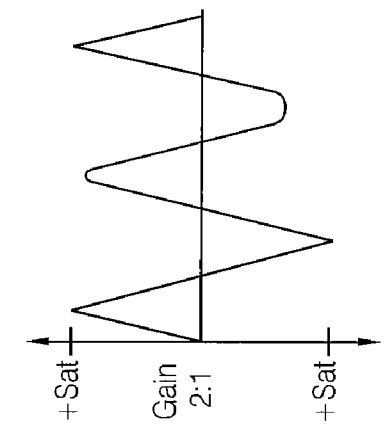
Figure 1C:
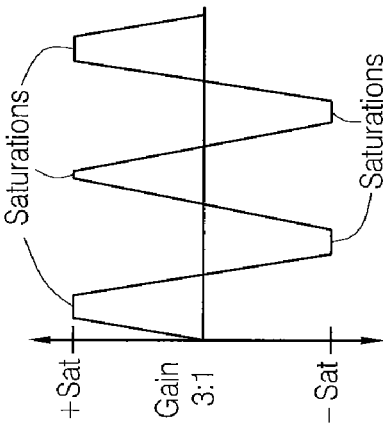
Figure 1B:
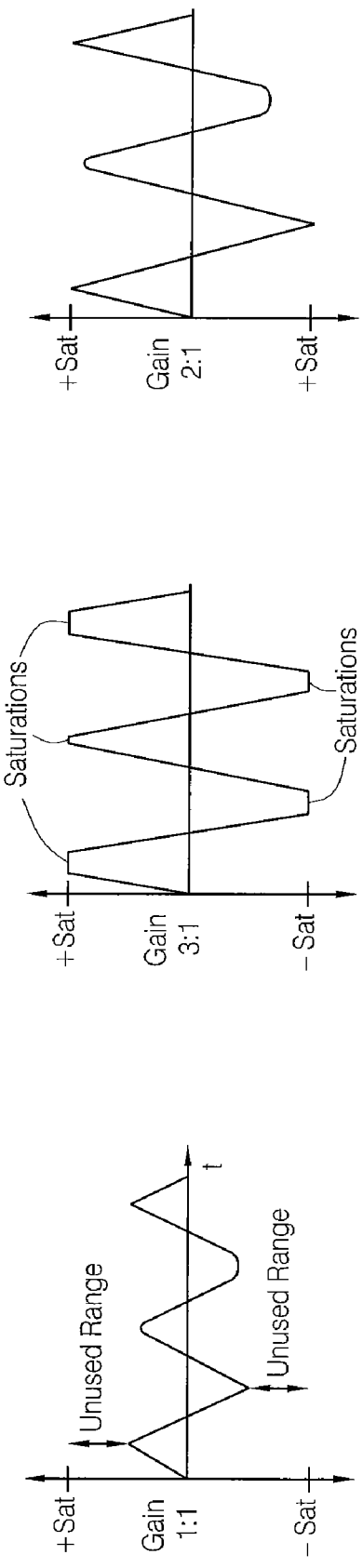

FIGS. 1B, 1C and 1D illustrate the base signal after having been amplified at various gain settings. It should be understood that the gain settings indicated are for illustration with ease of understanding and that in actual application amplifier gains are typically on the order of one to three orders of magnitude. FIG. 1B illustrates a unitary or one to one gain of the base signal illustrated in FIG. 1A. FIG. 1B also indicates a positive and a negative saturation level which in this embodiment is approximately twice the maximum amplitude of the base signal for the illustrated interval. Thus, the difference between the positive or negative saturation level and the local maxima of the base signal constitutes unused dynamic range with this particular gain setting. As previously noted, it is generally preferred to utilize a substantial portion of the dynamic range available and thus FIG. 1B illustrates a circumstance wherein a more aggressive gain setting may be indicated.

Conversely, FIG. 1C illustrates another embodiment wherein the amplifier gain is set to a 3:1 amplification ratio. It is assumed that the absolute positive and negative saturation levels remain the same. It can be seen that under this much more aggressive gain setting, that repeated instances of amplifier saturation occur at the higher positive and negative amplitudes of the base signal. As can be seen in FIG. 1B, the fidelity of the base signal is at least partially lost as, in the saturation intervals, the amplified signal no longer maintains the morphology of the unamplified base signal. Thus the fidelity of the amplified signal is degraded as the amplified signal is not able to proportionally track the base signal.

FIG. 1D illustrates a more preferably individualized or "optimized" gain setting in this illustrative example. More particularly, the illustrated gain setting of 2:1 utilizes a more substantial portion of the available dynamic range, however, avoids the saturation intervals exhibited in the embodiment illustrated in FIG. 1C. Thus, FIG. 1D illustrates the general concept of gain optimization. Again, as used herein, optimization is a relative term indicating the improved performance for an individual variable system. Optimization does not imply that no further improvement is possible or that the performance of the system is ideal under all possible circumstances.

Figure 2B:
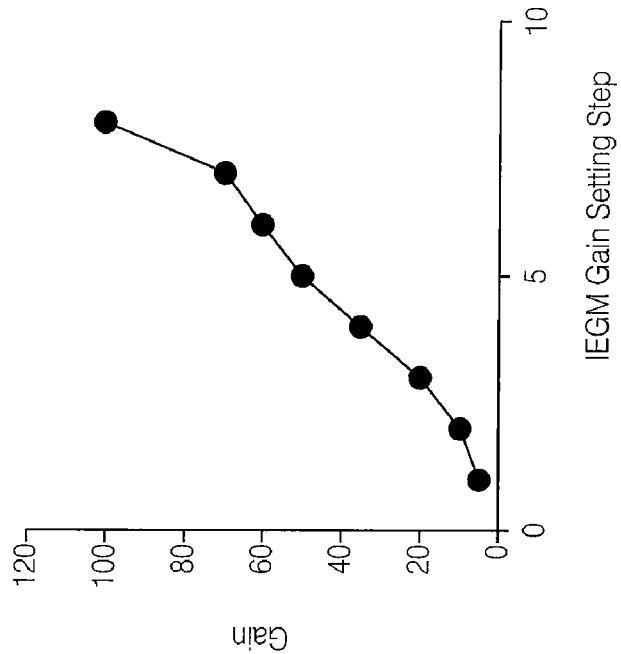
FIGS. 2A and 2B illustrate two exemplary graphs of iterative gain adjustment for sensing a relatively narrow and wideband signal respectively.
Figure 2A:
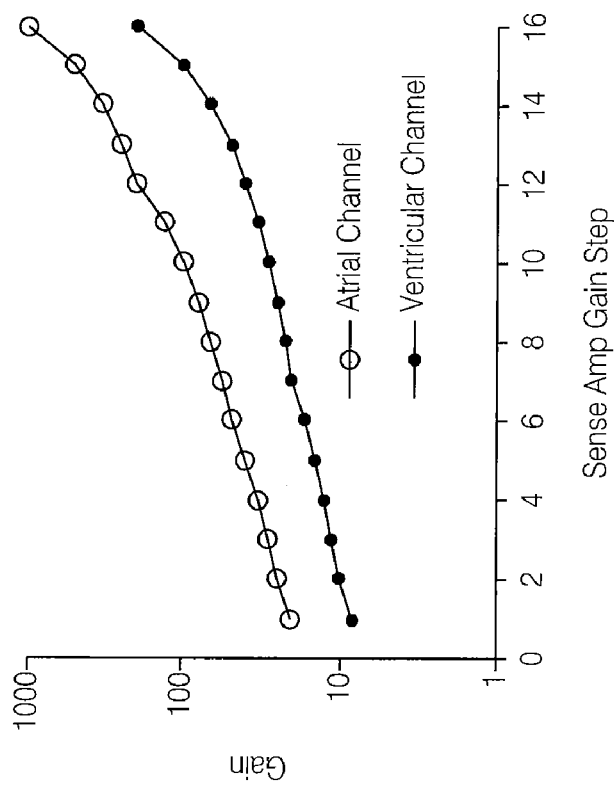

FIGS. 2A and 2B illustrate schematically one embodiment of a process for adjusting or optimizing the gain of an amplifier and the sensing system. FIG. 2A illustrates a step-wise method of adjusting the amplifier gain through a plurality of adjustments steps (in this embodiment 16 steps) to achieve a more optimal or individualized gain setting. The gain is indicated on a logarithmic scale from 1-1000. FIG. 2A also shows separate gain settings for a plurality of the sensing channels. This embodiment comprises an atrial channel and a ventricular channel with the atrial channel having higher gain settings. Through a series of iterative steps, the gain is progressively increased in steps of approximately 11% until a more appropriate gain setting for the particular configuration is achieved. In this embodiment, this iterative gain setting and evaluation takes 16 adjustment steps or iterations. In this embodiment, five separate measurements are performed per step which each measurement taking approximately one second. Thus, in this embodiment, the overall gain adjustment or optimization process takes over a minute to perform. The sensing channels and corresponding gain adjustment indicated in FIG. 2A corresponds to what is generally considered a narrow band sensing system.

In comparison, the embodiment illustrated in FIG. 2B corresponds to what is generally considered a wide band sensing system. In one particular embodiment, as illustrated in FIG. 2B, the respective sensing and gain adjustments are illustrative of an intracardiac electrogram (IEGM). As the embodiment illustrated in FIG. 2B corresponds to a relatively wider band sensing system, the gain adjustment per step is relatively larger, in this embodiment approximately 20%. The relatively small steps in the gain adjustment in either case are selected to avoid loss of sensing occurring during the sensing adjustment process. However, as previously described, the intervals during which the various sensing gains are adjusted constitutes dead time for the physician during the implantation process leading to inconvenience and inefficient use of the highly skilled professional's time. Thus a need exists for improvements in the sensing adjustment process while maintaining the quality of the resulting individualization adjustment.

Figure 3B:
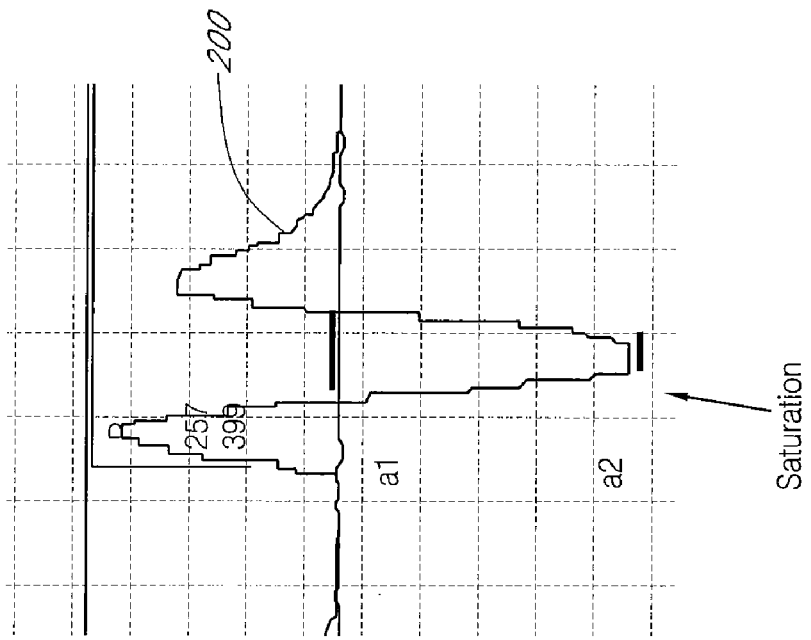
FIGS. 3A and 3B illustrate exemplary waveforms of amplified cardiac depolarization signals with little or no amplifier saturation and distinct saturation respectively and waveform characteristics or parameters which can be utilized to improve gain adjustment.
Figure 3A:
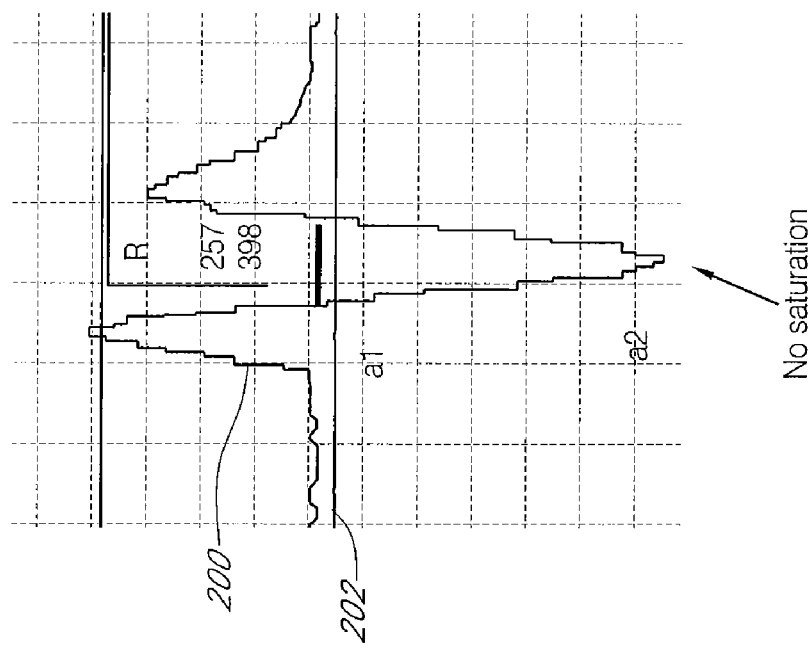

FIGS. 3A and 3B illustrate in greater detail a representative or exemplary physiologic signal 200 which can be sensed by an implantable device 10 described in greater detail below with references to FIGS. 12 and 13. In this particular embodiment, the physiologic signal 200 corresponds to sensed cardiac depolarization signals frequently referred to as the PQRST complex. FIGS. 3A and 3B also indicate that certain parameters or characteristics of the physiologic signal 200 can be designated and evaluated.

In this embodiment, a baseline 202 is defined partitioning positive signal polarities from negative signal polarities. This embodiment also defines a baseline crossing width A1 defined as the relative width or time interval between the signal 200 crossing the baseline 202 at one or more characteristic portions of the signal 200. In one particular embodiment as illustrated in FIGS. 3A and 3B, the baseline crossing width A1 corresponds to the duration or interval of the R wave associated with ventricular depolarization. A saturation width A2 is also defined in this embodiment. The saturation width A2 is defined as an interval or duration during which the signal 200 as amplified at the current gain setting or adjustment may or may not saturate. For example, FIG. 3A illustrates that the saturation width A2 has a substantially zero width or duration as the sensed signal 200 with the current gain settings of the amplifier exhibits substantially no saturation. In contrast, as illustrated in FIG. 3B, an observable saturation width A2 is present under the illustrated conditions of the characteristics of the signal 200 and the current gain setting of the amplifier resulting in a duration of amplifier saturation. In this embodiment, the measured or determined values of the baseline crossing width A1 and saturation width A2 are utilized to calculate a saturation ratio (SR) which is indicative of the adjustment required in a current gain setting to achieve more desirable sensing performance.

Figures 4, 5:
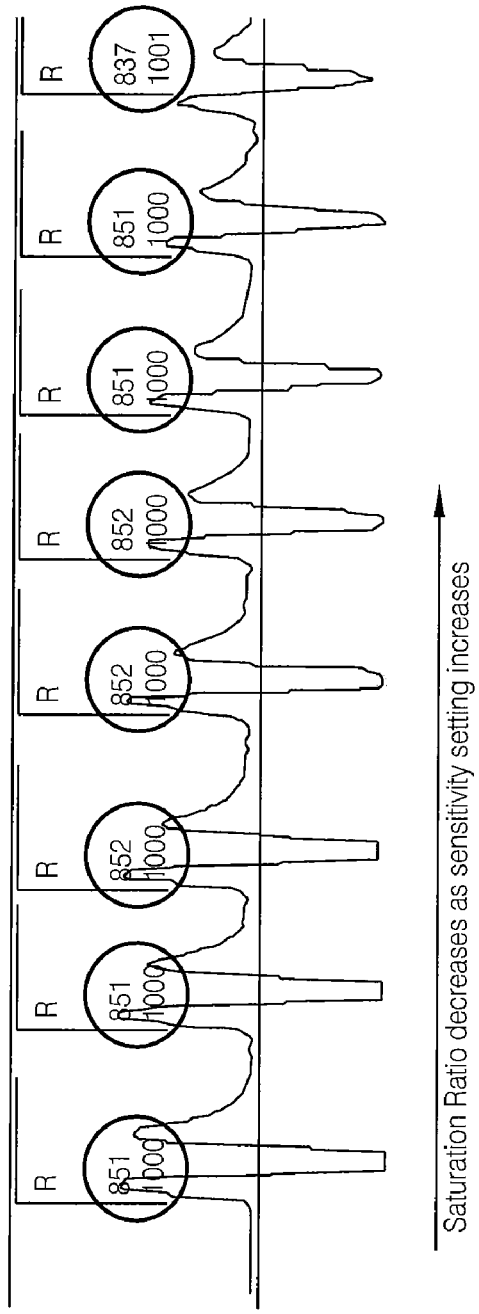
FIG. 4 illustrates one embodiment of a system and method of gain adjustment indicated by an exemplary look-up table of saturation ratio ranges with corresponding gain adjustment steps.
FIG. 5 illustrates one embodiment of a sequential gain setting procedure showing the sequential reduction and eventual elimination of amplifier saturation.

FIG. 4 illustrates one example of an implementation based in part on an analysis or evaluation of the saturation ratio SR to accelerate a gain adjustment process. More particularly, FIG. 4 illustrates a look-up table correlating various ranges of saturation ratios and corresponding indicated gain adjustments. In one embodiment, the saturation ratios are partitioned into five ranges of values partitioned as saturation ratios of 0, 0-30%, 31%-60%, 61%-85%, and 86%-100%. The larger saturation ratios SR indicate that a larger proportion of the signal 200 is causing the amplifier to saturate and thus indicates that relatively larger adjustments in the gain setting are indicated. In this particular example, a number of gain adjustments steps to be adjusted are selected based in part on the observed or measured saturation ratio SR. More particularly, a saturation ratio SR of 0 is interpreted that no adjustment is indicated or that the current individualized setting of the gain in the sensing system is appropriate for the individual conditions. A saturation ratio of between >0 and 30% is interpreted as indicating a single step in the gain adjustment. Saturation ratios of 31%-60%, 61%-85%, and/or 86%-100% are interpreted as indicating that respectively more aggressive adjustment of a current gain setting can be safely implemented in a single iteration of adjustment with relatively low likelihood of loss of sensing occurring. In this embodiment, saturation ratios of 31%-60%, 61%-85%, and 86%-100% would result in gain adjustments of 2, 3, and 4 steps in a single iteration, respectively. Thus, larger saturation ratios SR are evaluated as indicating that the relative degree of saturation of the amplification of the signal 200 is such that one or more intermediate gain adjustment steps can be safely skipped over without significant risk of losing sensing. Alternatively, the step number N can be calculated as N=(round down integer) $S^\alpha/F^\beta$, where F, $\alpha$, $\beta$ are coefficients, with typical values F=0.25, $\alpha$=1, $\beta$=1 for this embodiment.

FIG. 5 illustrates a further embodiment of a signal 200 corresponding to relatively narrow band sensing over eight cardiac cycles. The gain/sensitivity is iteratively adjusted and the morphology of the amplified sensed signal 200 as well as the sequence of signal markers illustrates the changes in the sensing with the progressively adjusted gain/sensitivity. The sequential sensing of the signal 200 with the iteratively adjusted gain/sensitivity settings proceeds from left to right as illustrated in FIG. 5. As can be seen with the initial sensitivity settings, the signal 200 fairly strongly saturates resulting in a relatively large saturation ratio. The morphology of the amplified signal 200 at peak signal amplitude exhibits degraded fidelity as the sensing system saturates and thus exhibits a flat or constant amplified signal 200. Thus the amplified signal 200 does not accurately correspond to the underlying physiologic activity in these regions. This is also indicated with the initial signal markers indicating repeated successive instances of substantially identical markers.

Figure 7:
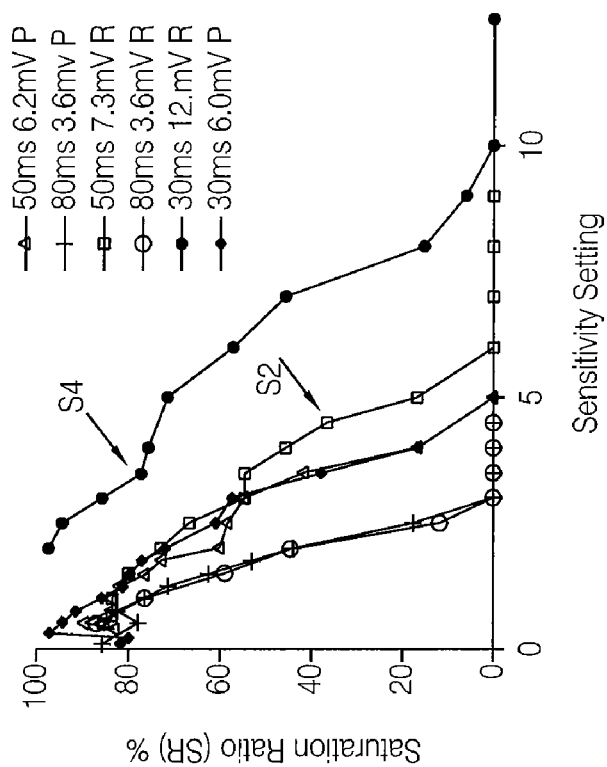
FIG. 7 is another exemplary graph of a plurality of saturation ratio-vs.-sensitivity settings with various signal amplitudes and widths.
Figure 6:
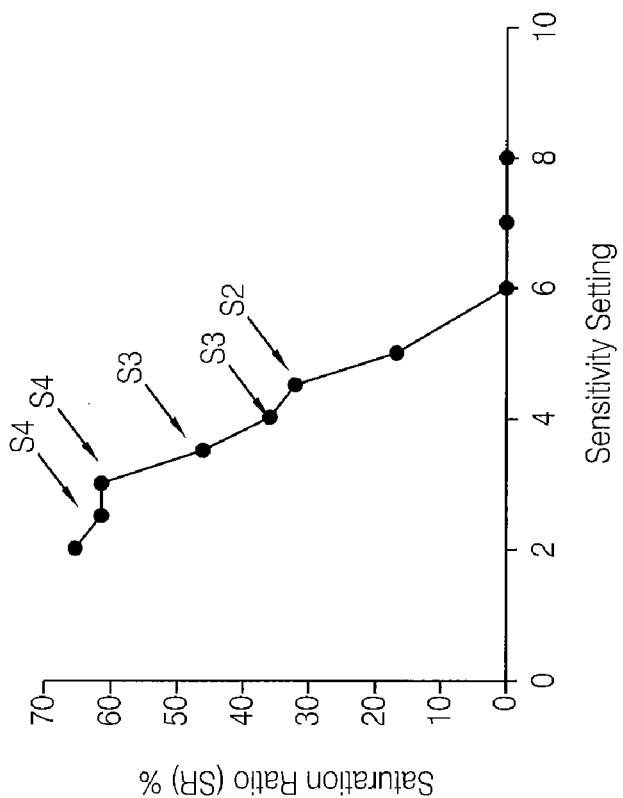
FIG. 6 is an exemplary graph of one embodiment of decreasing saturation ratios with successive gain adjustments.

However, as the sensitivity/gain is iteratively adjusted, it can be seen that the saturation decreases as the sensitivity setting increases. At the last illustrated complex of the signal 200, it can be seen that substantially no saturation is occurring, the morphology of the signal 200 corresponds to that expected for the underlying physiologic activity. The collected morphology data are apparently different with and without saturation with the similar signals FIG. 6 illustrates an exemplary embodiment of a plot of saturation ratio indicated as a percentage versus a plurality of sensitivity settings corresponding to those illustrated in FIG. 5. As shown in FIG. 6, the initial sensitivity setting results in a relatively high saturation ratio of approximately sixty-five percent. As the sensitivity setting is progressively increased (gain decreased), the saturation ratio drops until, in this embodiment, the eighth iteration, wherein the saturation ratio falls to substantially zero resulting in accurate amplification of the signal 200 with little to no influence of saturation on the signal fidelity. FIG. 6 also illustrates that with relatively high saturation ratios, a prediction can be made that multiple sensitivity setting steps can be made at once, e.g., skipped-over, with relatively low risk of losing sensing but so as to accelerate or reduce the time required to achieve an appropriate sensitivity setting. FIG. 7 illustrates similar information as FIG. 6, however with multiple embodiments of various narrow band signal sensing, such as of P or R waves and of various signal amplitudes and widths.

Figure 8B:
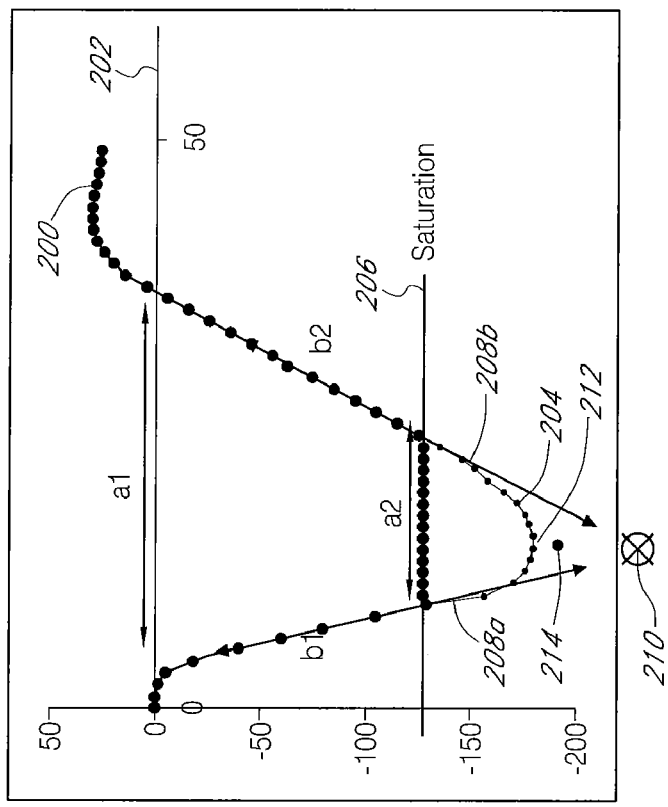
FIGS. 8A and 8B illustrates one embodiment of a gain setting method employing saturation and amplification estimation with more and less severe saturation respectively.
Figure 8A:
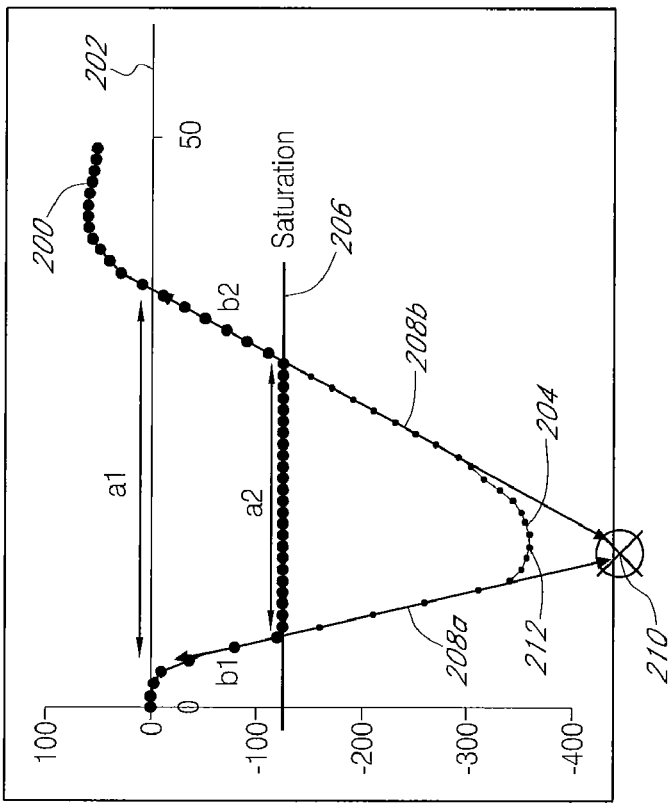

FIGS. 8A and 8B illustrate further embodiments of a system and method to accelerate gain adjustment in sensing systems. The embodiments illustrated with respect to FIGS. 8A and 8B are generally adapted for use with relatively wideband sensing systems, for example systems adapted to sense IEGM signals. Relatively wideband signals generally exhibit less steep signal slopes than narrowband signals. FIGS. 8A and 8B illustrate embodiments wherein the sensing system is currently configured with inadequate sensitivity/excessive gain with FIG. 8A illustrating more severe saturation and FIG. 8B illustrating less severe saturation.

In a similar manner to the embodiments previously described, a baseline 202 is defined for the signal 200 separating positive and negative polarities of the time varying signal 200. A baseline crossing width A1 and a saturation width A2 are also characteristics of the signal 200 defined in a similar manner as that previously described. FIGS. 8A and 8B also illustrate schematically in broken lines that a lost signal portion 204 exists during the period when the amplified signal 200 is saturated, e.g., during the saturation width or interval A2. The lost signal portion 204 illustrates the morphology and amplitude of the amplified signal 200 if the dynamic range of the amplifier system were not exceeded.

FIGS. 8A and 8B also illustrate additional characteristics or parameters of the signal 200 which can be utilized in certain embodiments to facilitate individualizing or optimizing the amplifier gain/sensitivity setting for more accurate sensing of the signal 200. In one embodiment, the signal 200 can be approximated in certain regions of the signal 200 by line segment portions indicated as B1 and B2. The linear segment regions B1 and B2 correspond to portions of the signal 200 wherein the time rate of amplitude change is approximately linear. The linear segment portions B1 and B2 approximate the signal 200 as linear segments extending between the baseline 202 and the saturation level 206. The linear segments B1 and B2 can be extended or extrapolated along extension portions 208A and 208B respectively which also approximate the signal 200 along part of the lost signal region 204. The extension regions 208A and 208B can be considered to intersect at an intersection point 210 which comprises an approximation of the amplitude peak of the signal 200 in the lost signal region 204. Because of the expected curvature of the signal 200 at the peak amplitude 212, the intersection point 210 would generally exhibit a higher amplitude than the true peak amplitude 212 of the signal 200.

FIG. 8A illustrates that with relatively higher saturation ratios, e.g. in embodiments wherein the lost signal region 204 comprises a more substantial portion of the signal 200 which extends beyond the saturation level 206, the approximation of the intersection point 210 is a less accurate approximation of the peak amplitude 212. In contrast, as illustrated in FIG. 8B, when the saturation ratio SR is relatively low, e.g. wherein the saturation width A2 is relatively narrow or short as compared to the baseline crossing width A1, the intersection point 210 is a more accurate approximation of the peak amplitude 212. In applications wherein the characteristics and morphology of the signal 200 are relatively uniform and predicable, an attenuation factor can be provided to account for the expected curvature of the signal 200 near the peak amplitude 212 to provide a more accurate estimate of the peak amplitude 212.

Thus in one embodiment, the signal 200 is evaluated with respect to the baseline 202 and saturation level 206 to determine a baseline crossing width A1 and a saturation width A2. The baseline crossing width A1 and saturation width A2 can then be evaluated to determine a saturation ratio SR equal to A2 divided by A1. If the saturation ratio SR is less than a threshold, in one embodiment less than 50%, a determination is made to estimate a peak amplitude 212 of the signal 200 in the presence of saturation. Linear segments B1 and B2 are determined along with corresponding extension segments 208A and 208B. The intersection point 210 is then determined as the intersection of the extension segments 208A and 208B. An attenuation factor can then be applied to the intersection point 210. In one embodiment an attenuation factor of between 0.5 to 0.75 is utilized to determine an estimated signal peak 214. The gain of the amplifier system is then adjusted or optimized based on the estimated signal peak 214 directly to thereby avoid the stepwise iterative adjustment and remeasuring for example of the embodiment illustrated with respect to FIG. 2B. In other embodiments, the intersection point 210 is itself utilized as an estimate for the signal peak 212 to provide a safety margin in the adjustment of the amplifier sensitivity. Likewise, the attenuation factor utilized to determine the estimated peak 214 can similarly be adjusted or programmed to provide an appropriate safety margin. The appropriate selection of these values will be well understood by one of ordinary skill considering the requirements of a particular application.

Figure 9:
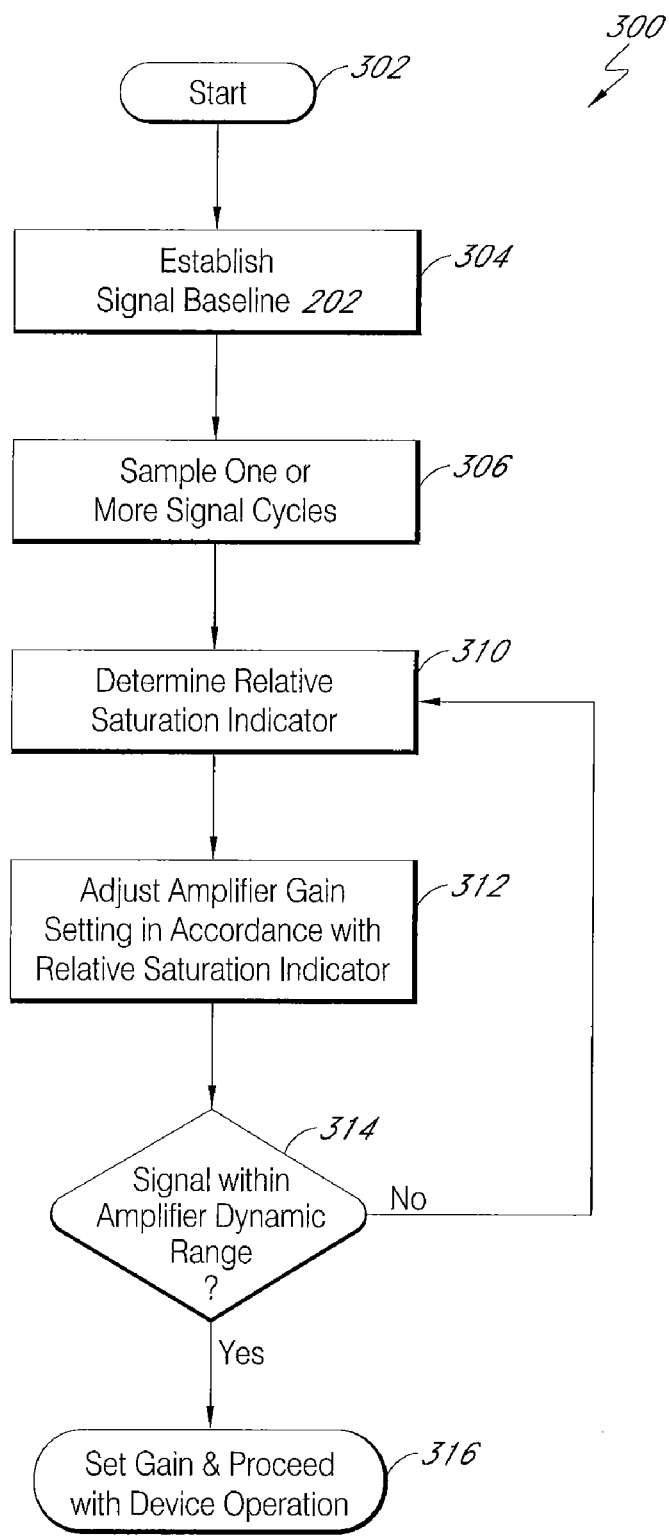
FIG. 9 is a flowchart of one embodiment of an improved method of adjusting amplifier gain adapted for relatively narrowband sensing.

FIG. 9 illustrates a flow chart of one embodiment of a method 300 for adjusting or optimizing amplifier gain/sensing. The method 300 is applicable to a variety of sensing systems. However, the method 300 is particularly useful with implantable cardiac stimulation device systems adapted for relatively narrowband sensing. The method 300 begins in a start block 302. In one embodiment, the start block 302 comprises an implantation and programming procedure of an implantable cardiac stimulation device 10 and programming of the device 10 by a physician and/or other attending clinical personnel with use of an external device 120 such as a physician's programmer (see FIGS. 12 and 13 and following associated detailed description). In one embodiment, the start block 302 would also include implantation of one or more sensing electrodes in at least an initial location and would typically include evaluation of signals provided by the one or more sensing electrodes as well as adjustment of sensing sensitivity or gain for the particular configuration of implantable device 10 as provided to the individual patient. Embodiments of the method 300 are at least partly directed to improvements in the evaluation and adjustment of sensing provided by the device 10.

Following from the start block 302 occurs a block 304 wherein the signal 200 is sensed and the signal baseline 202 is established. Again the baseline 202 separates positive from negative polarities of the signal 200. Following from the establishment of the signal baseline 202 and block 304, a block 306 follows wherein one or more cycles of the signal 200 are sampled. Following the sampling of block 306, an evaluation/determination is made in a block 310 to determine a relative saturation indicator. The determination of block 310 establishes a relative measure of the amount of amplifier saturation occurring at the present amplifier gain setting. This embodiment of the method 300 assumes that the amplifier gain is initially set at a relatively high level to avoid undersensing. That is, the sensitivity parameter is initially set at a relatively low number for the given configuration of the device 10 and the individual patient such that at initial programming of the device 10 at least periods of amplifier saturation would be expected.

Following from determination of block 310, a decision block 314 follows wherein an evaluation is made whether the signal falls within the available amplifier dynamic range, e.g. if amplifier saturation is substantially absent. If the decision of block 314 is negative, e.g. the available dynamic range is being exceeded as exhibited by amplifier saturation, a block 312 follows wherein the amplifier gain setting/sensitivity is adjusted in accordance with the relative saturation indicator determined in block 310. As previously noted, embodiments of the method 300 are at least partly adapted to accelerate or increase the speed and adjustment process of the amplifier. Depending on the particular conditions of a given application, the adjustment of block 312 can achieve satisfactory amplifier adjustment in a single iteration.

If the decision of block 314 is again negative, the method 300 returns to blocks 310 and 312 in an iterative manner to be followed by further decision(s) of block 314. If however the decision of block 314 is affirmative, a block 316 follows wherein the adjustment made in any previous block(s) 312 is programmed or set in the device 10 and further programming/operation of the device 10 proceeds in a conventional manner.

Figure 10:
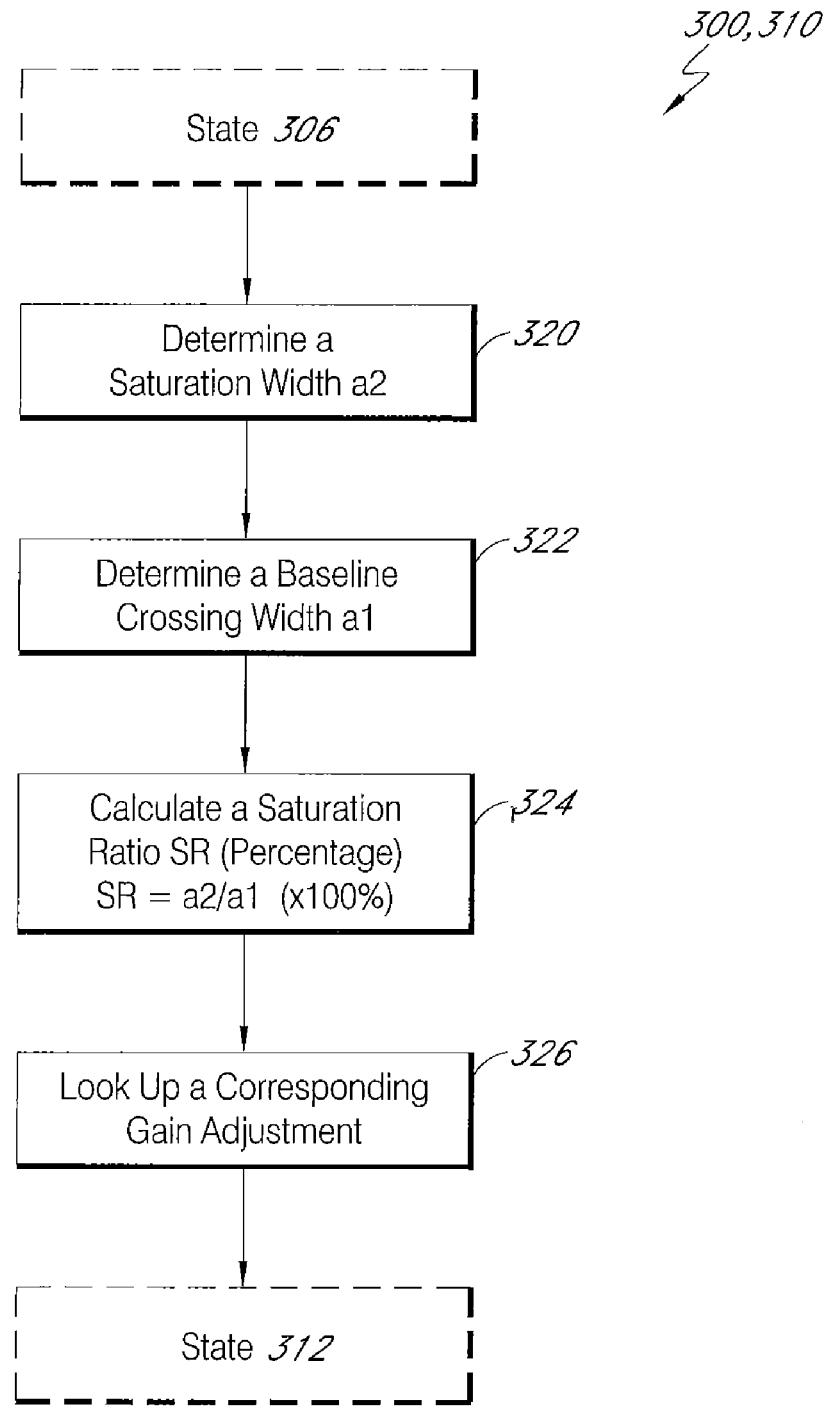
FIG. 10 is a more detailed flowchart of a portion of the embodiment illustrated in FIG. 9.

FIG. 10 illustrates in greater detail one embodiment of the method 300 and more particularly the determination or evaluation of block 310. In this embodiment, following from block 306, a measurement or determination is made in block 320 of a saturation width A2. Again as previously described the saturation width A2 is the duration or length of time that the amplifying system is saturated by the signal 200. A block 322 also occurs wherein a determination or measurement is made of a baseline crossing width A1. Then a block 324 occurs wherein a calculation is made of a saturation ratio SR defined as the ratio of the saturation width A2 to the baseline crossing width A1. The saturation ratio SR is indicative of the relative degree with which the amplifier system is saturating under existing conditions, e.g. the sampling of block 306. Following from block 324 occurs a gain adjustment determination block 326 which in this embodiment comprises looking up an indicated gain adjustment from a look up table based on the saturation ratio calculated in a block 324. The determination of block 326 facilitates establishing a variable gain adjustment that is made to the sensing system determined at least partially as a function of the relative degree within which the sensing system is experiencing saturation. Then following the block 326 would occur the previously described adjustment of block 312.

Figure 11:
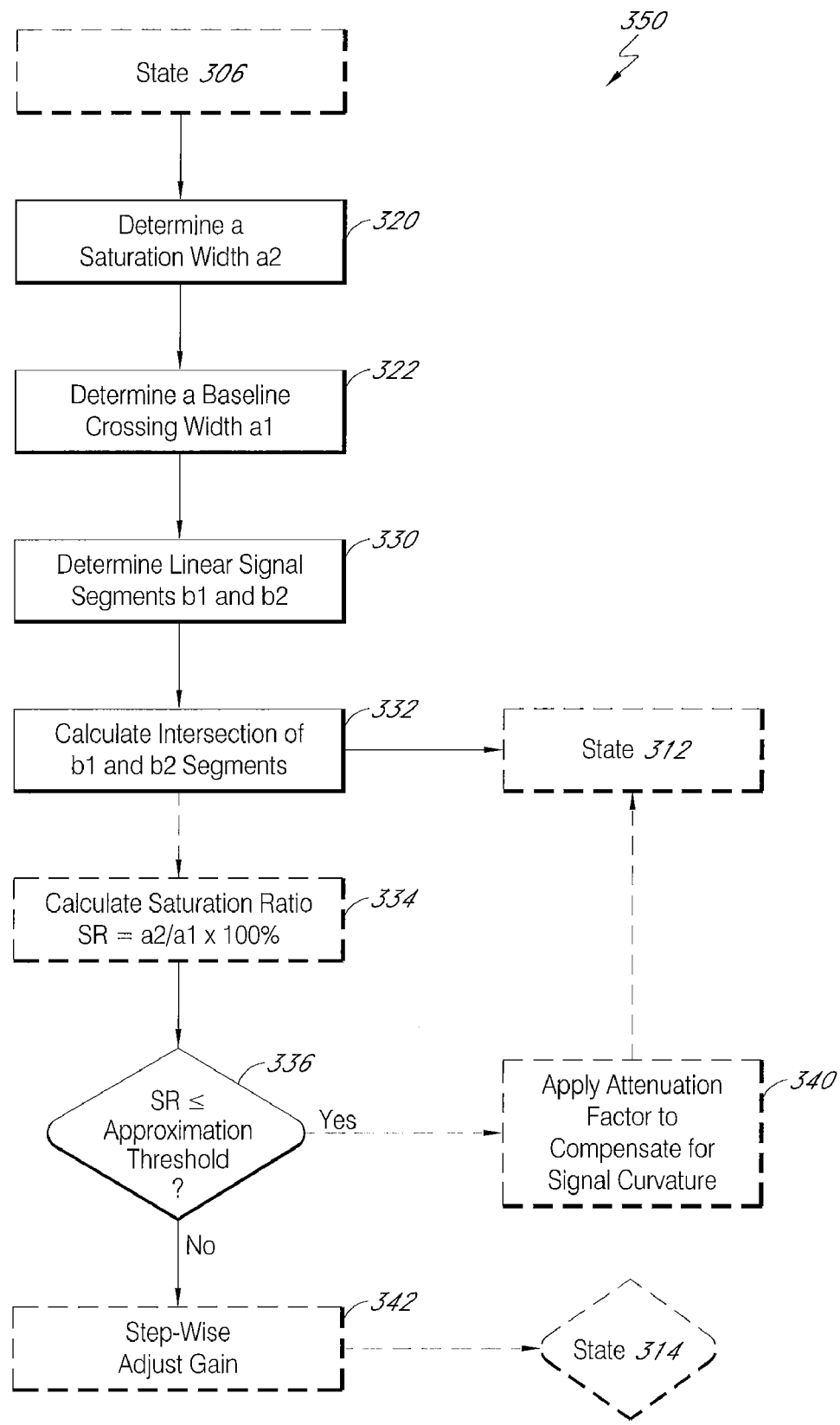
FIG. 11 is a flowchart of one embodiment of an improved method of adjusting amplifier gain adapted for relatively wideband sensing.

FIG. 11 illustrates another embodiment of a method 350 for adjusting or optimizing a sensing system. The method 350 is generally adapted for adjustment of relatively wide band sensing systems as opposed to the previously described embodiments of the method 300 which are more preferably employed with relatively narrow band sensing systems. The methods 300 and 350 share similarities up to block 306, the detailed description of which will not be repeated for brevity. In this embodiment, however, the method 350 proceeds from block 306 to a block 320 wherein a saturation width A2 of the signal 200 is determined. A block 322 also occurs wherein a baseline crossing width A1 is determined in a block 322. In this embodiment, the method 350 also includes a block 330 wherein linear signal segments B1 and B2 are determined or identified.

An estimation calculation is then performed in a block 322 to determine an intersection of the linear signal segments B1 and B2. This can include the determination of the previously described extension segments 208A and 208B with the intersection point 210. In one embodiment of the method 350, the calculated intersection from block 332 is used directly as a factor for the amplifier adjustment of the previously described block 312 which can be adjusted proportionally with respect to the calculated intersection from block 332 with an appropriate sensing safety margin.

In another embodiment, an optional branch including a block 334 follows wherein a calculation is made of the saturation ratio SR defined as equal to the ratio of the saturation width A2 to the baseline crossing width A1. A decision block 336 then follows wherein a decision is made whether the saturation ratio is within a selected approximation threshold. If the evaluation of block 336 is affirmative, an evaluation is made that the initial sensing parameters are such that the calculated intersection from block 332 is an appropriate approximation to the true peak signal amplitude 212 and a block 340 follows wherein an appropriate attenuation factor is applied to compensate for the curvature of the signal 200 at the peak amplitude 212. Following from block 340 would then proceed the adjustment block 312 as previously described.

If however the decision of block 336 is negative, e.g. that the saturation ratio SR is not within the selected approximation threshold, a block 342 follows wherein a stepwise adjustment is made to the amplifier gain for example as in the previously described method 300. The block 342 would then be followed by the decision of the previously described block 314 and the adjustment of block 342 may proceed in an iterative manner depending upon the particular characteristics and configuration of the device for the individual patient.

Figure 12:
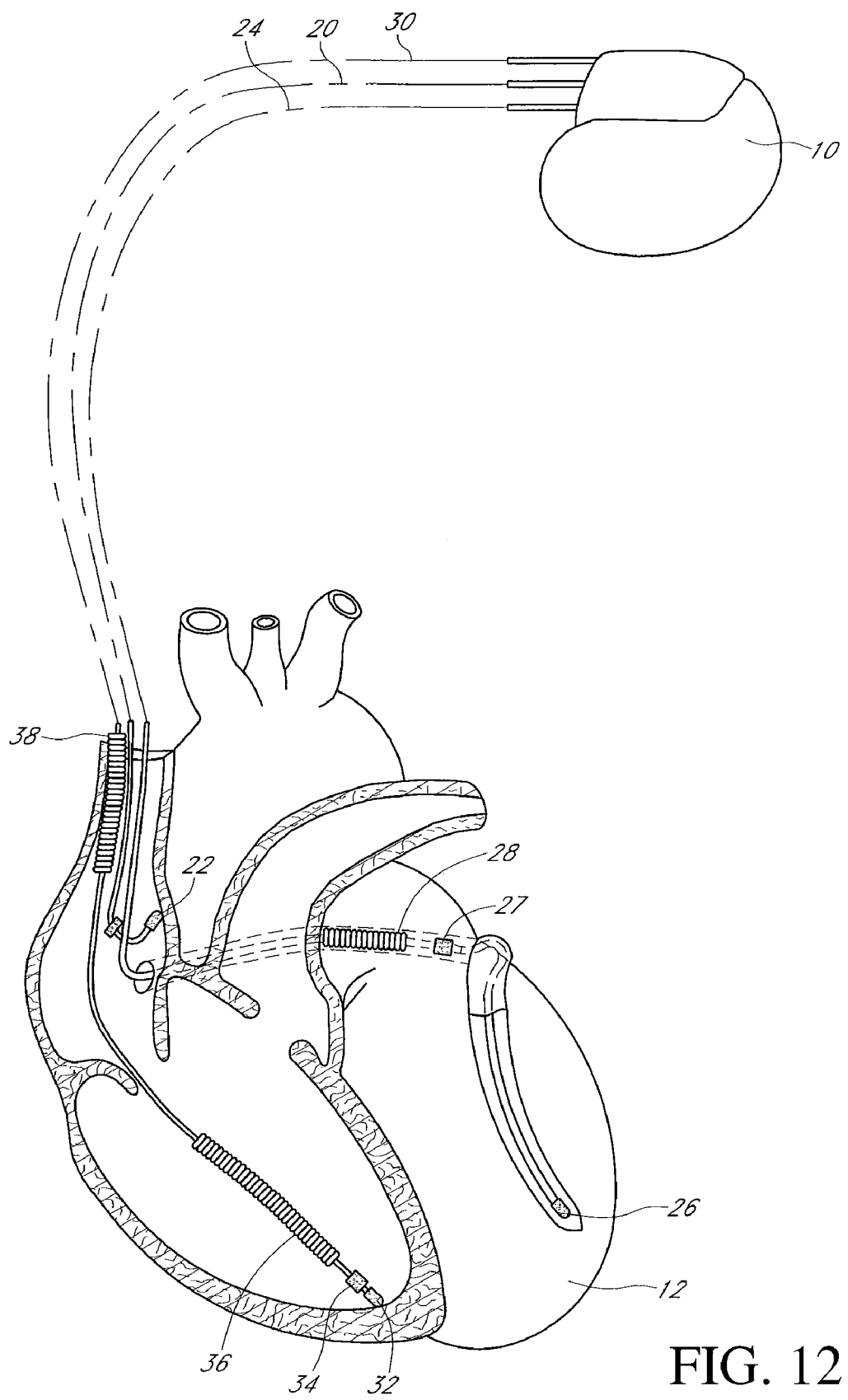
FIG. 12 is a simplified diagram illustrating an implantable stimulation device in electrical communication with at least three leads implanted into a patient's heart for delivering multi-chamber stimulation and shock therapy.
Figure 13:
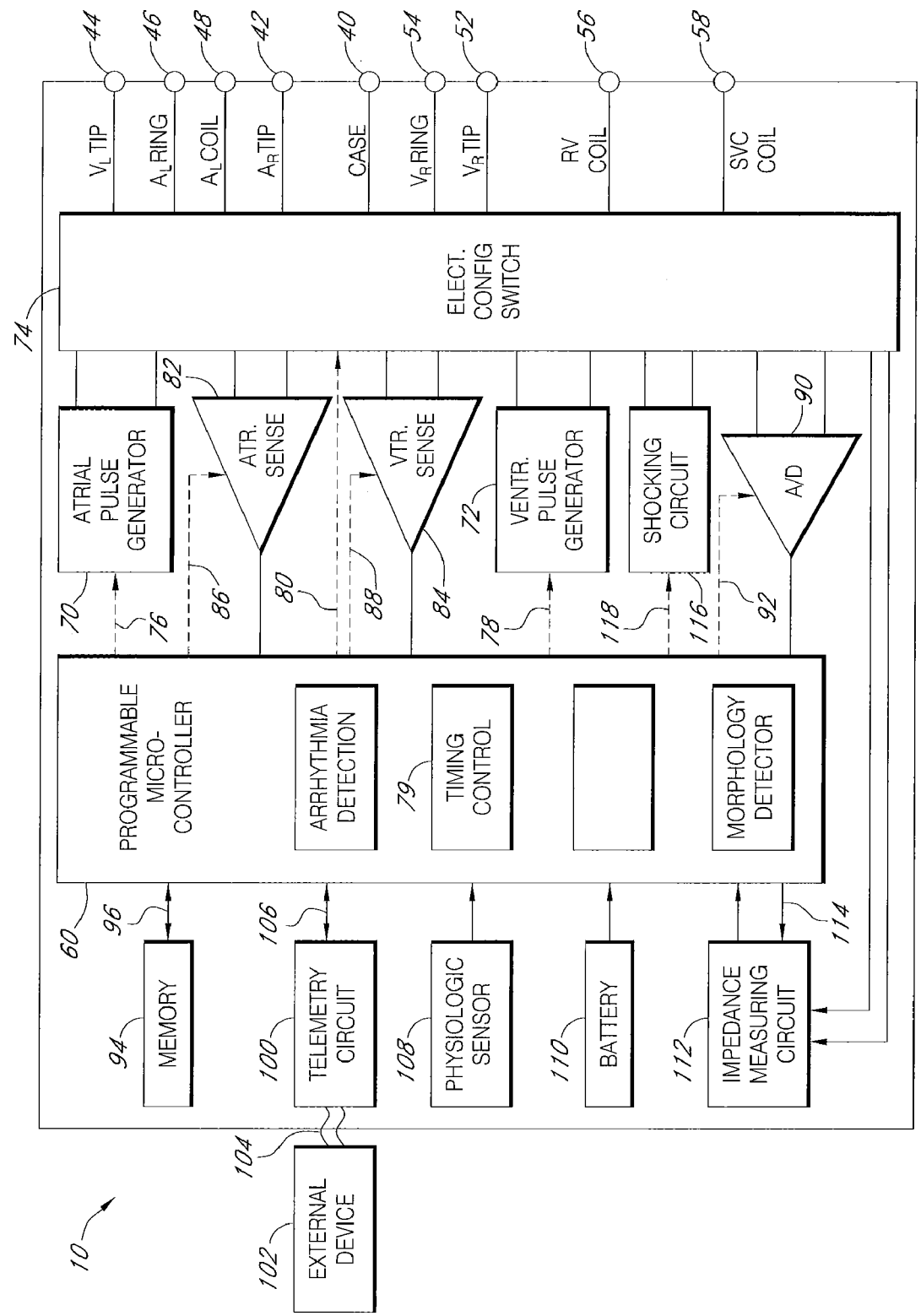
FIG. 13 is a functional block diagram of a multi-chamber implantable stimulation device system illustrating the basic elements of a stimulation device which can provide cardioversion, defibrillation and pacing stimulation in four chambers of the heart in communication with an external device, such as a physician's programmer.

FIGS. 12 and 13 illustrate embodiments of a device 10 which can advantageously employ the previously described embodiments for setting/adjusting amplifier gain. In one embodiment, as shown in FIG. 12, a device 10 comprising an implantable cardiac stimulation device 10 is in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

As illustrated in FIG. 13, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 13, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 13, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows IEGMs and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 13. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, embodiments of the device 10 including shocking capability preferably employ lithium/silver vanadium oxide batteries. For embodiments of the device 10 not including shocking capability, the battery 110 will preferably be lithium iodide or carbon monoflouride or a hybrid of the two.

As further shown in FIG. 13, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims, where claim language carries an ordinary meaning as in customary usage and not by special definition unless specifically stated as providing a definition.

What is claimed is:

1. An implantable medical device system comprising:
   an implantable sensing electrode configured to sense one or more physiologically based signals;
   at least one signal amplifier receiving the physiologically based signals and amplifying these signals by an adjustable amplifier gain; and
   a controller receiving the amplified signals and evaluating a patient's condition as indicated by the amplified signals, wherein, following an initial implantation, the amplified signals are evaluated and a saturation indicator is calculated and wherein the amplifier gain is adjusted as a function of the saturation indicator so as to inhibit saturation of the signal amplifier with larger saturation indicators resulting in larger gain adjustments;
   wherein the saturation indicator is calculated as a ratio of duration of saturation of the at least one signal amplifier to a duration between corresponding zero crossings of a signal baseline.

2. The system of claim 1, wherein the signal amplifier is adjustable by discrete gain settings and wherein one or more of the discrete gain settings are set in the amplifier adjustment.

3. The system of claim 1, further comprising a programmer in communication with the controller and wherein the programmer performs the evaluation of the amplified signals and provides commands to the controller to adjust the amplifier gain as indicated.

4. The system of claim 1, comprising a first and a second signal amplifier wherein the first signal amplifier is configured for narrower band sensing and the second signal amplifier is configured for wider band sensing with different gain settings for the first and second signal amplifiers.

5. The system of claim 4, wherein the first signal amplifier is configured as one of an atrial or ventricular sensing channel and the second signal amplifier is configured to sense an intracardiac electrogram of evoked cardiac response.

6. An implantable medical device system comprising:
   an implantable sensing electrode configured to sense one or more physiologically based signals;
   at least one signal amplifier receiving the physiologically based signals and amplifying these signals by an adjustable amplifier gain; and
   a controller receiving the amplified signals and evaluating a patient's condition as indicated by the amplified signals, wherein, following an initial implantation, the amplified signals are evaluated and a saturation indicator is calculated and wherein the amplifier gain is adjusted as a function of the saturation indicator so as to inhibit saturation of the signal amplifier with larger saturation indicators resulting in larger gain adjustments;
   wherein the saturation indicator is calculated at least partly based on an extrapolated intersection of adjacent upward going and downward going signal segments.

7. A method of selecting an appropriate gain setting for a signal amplifier for an implanted cardiac stimulation device, the method comprising:
   (i) receiving a signal indicative of function of a patient's heart wherein the signal is amplified by an amplifier of the implanted cardiac stimulation device;
   (ii) selecting at least one characteristic of the signal and calculating a saturation parameter based upon the at least one selected characteristic of the signal;
   (iii) automatically determining a gain adjustment value that correlates, at least in part, to the magnitude of the saturation parameter; and
   (iv) adjusting the gain of the amplifier by the gain adjustment value;
   wherein receiving a signal indicative of the function of the patient's heart comprises receiving an IEGM signal and wherein selecting the at least one characteristic of the signal comprises selecting a curve of the IEGM signal that corresponds to a depolarization event of the heart; and
   wherein automatically calculating the saturation parameter comprises:
   processing the signal to determine a magnitude of a baseline crossing width of the selected curve of the IEGM signal;
   processing the signal to determine the magnitude of a saturation width of the selected curve of the IEGM signal; and
   determining a ratio between the saturation width and baseline crossing width.

8. The method of claim 7, further comprising repeating acts (i) through (iii) until the saturation parameter indicates that the amplifier is no longer saturating when the heart signal is being received.

9. The method of claim 7, wherein selecting a curve of the IEGM signal indicative of the depolarization event comprises selecting a curve indicative of the R-wave.

10. A method of selecting an appropriate gain setting for a signal amplifier for an implanted cardiac stimulation device, the method comprising:
    (i) receiving a signal indicative of function of a patient's heart wherein the signal is amplified by an amplifier of the implanted cardiac stimulation device;
    (ii) selecting at least one characteristic of the signal and calculating a saturation parameter based upon the at least one selected characteristic of the signal;
    (iii) automatically determining a gain adjustment value that correlates, at least in part, to the magnitude of the saturation parameter; and
    (iv) adjusting the gain of the amplifier by the gain adjustment value;
    wherein receiving a signal indicative of the function of the patient's heart comprises receiving an IEGM signal and wherein selecting the at least one characteristic of the signal comprises selecting a curve of the IEGM signal that corresponds to a depolarization event of the heart; and
    wherein automatically calculating the saturation parameter comprises using saturation related values to approximate the peak value of the curve indicative of the polarization event.

* * * * *